(12) United States Patent
Coquerel et al.

(10) Patent No.: US 6,316,671 B1
(45) Date of Patent: Nov. 13, 2001

(54) METHOD FOR SPLITTING 1-AMINO-ALKAN-2-OL COMPOUNDS

(75) Inventors: Gerard Coquerel, Boos; Lionel Catroux, Poce sur Cisse; Yvette Combret, Rouen, all of (FR)

(73) Assignee: Universite de Rouen (FR)

( * ) Notice: Subject to any disclaimer, the term of this patent is extended or adjusted under 35 U.S.C. 154(b) by 0 days.

(21) Appl. No.: 09/322,527

(22) Filed: May 28, 1999

Related U.S. Application Data (63) Continuation of application No. PCT/FR97/02158, filed on Nov. 28, 1997.

(51) Int. Cl.⁷ .................................................. C07B 57/00
(52) U.S. Cl. ........................ 564/303; 564/302; 564/505
(58) Field of Search .................................... 564/453, 454, 564/462, 463, 497, 303, 302, 505

(56) References Cited

U.S. PATENT DOCUMENTS

| | | |
|---|---|---|
| 3,116,332 | * 12/1963 | Sullivan et al. . |
| 5,723,667 | * 3/1998 | Drauz et al. ........................ 564/302 |
| 5,986,135 | * 11/1999 | Pfrengle et al. ..................... 564/303 |

OTHER PUBLICATIONS

Drauz, Karlheinz et al, Chem. Eur J., 1(8), 538–540, 1995.*
Leonard et al, Chemical Abstract, vol. 115, No. 9. 91743, 1991.*

* cited by examiner

*Primary Examiner*—Shailendra Kumar
(74) *Attorney, Agent, or Firm*—Schnader Harrison Segal & Lewis LLP (57) ABSTRACT

This invention relates to a method of splitting 1-amino-alkan-2-ol compounds of general formula:

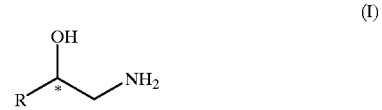

(I)

in which the group R can represent a wide variety of linear, branched or cyclic alkyl groups, comprising up to about 20 to 25 carbon atoms and preferably 1 to 15 carbon atoms. These groups can possibly have one or more double bonds, one or more hetero-atoms such as oxygen or sulfur so long as these are to be found separated from the asymmetric carbon atom by at least one carbon link and do not destroy the aliphatic nature of the group R. These groups can also be substituted by one or more halogen atoms such as chlorine or lower alkoxy groups such as methoxy or ethoxy groups.

23 Claims, 1 Drawing Sheet

Fig. 1

METHOD FOR SPLITTING 1-AMINO-ALKAN-2-OL COMPOUNDS

RELATED APPLICATION

This is a continuation of International Application No. PCT/FR97/02158, with an international filing date of Nov. 28, 1997, which is based on French Patent Application No. 96/14694, filed Nov. 29, 1996.

FIELD OF THE INVENTION

This invention relates to a method of splitting 1-amino-alkan-2-ol compounds of general formula:

(I)

in which the group R can represent a wide variety of linear, branched or cyclic alkyl groups, comprising up to about 20 to 25 carbon atoms and preferably 1 to 15 carbon atoms. These groups can possibly have one or more double bonds, one or more hetero-atoms such as oxygen or sulfur so long as these are to be found separated from the asymmetric carbon atom by at least one carbon link and do not destroy the aliphatic nature of the group R. These groups can also be substituted by one or more halogen atoms such as chlorine or lower alkoxy groups such as methoxy or ethoxy groups.

BACKGROUND

From an industrial point of view, the resolution of (±) chiral compounds is in most cases an advantageous alternative to the asymmetric synthesis of one of the enantiomers.

In the case of compounds of formula (I), resolution through biased crystallization can be carried out by several methods when R is an aryl group (1, 2). Syntheses of compounds of formula (I) in which R is an alkyl group, from chiral reactants have also been described (3 to 11). These syntheses do not represent a general method but are specified on a case by case basis and until now, resolutions based on a diastereoisomeric crystallization or a preferential crystallization have not resulted in a satisfactory outcome (12 to 18).

SUMMARY OF THE INVENTION

This invention is aimed precisely at providing a method of resolving salts by a selective crystallization, easy to implement, reproducible and permitting access to the two enantiomers with high enantiomeric purity, possibly greater than 99%.

This goal is achieved thanks to the formation of salts of 1-amino-alkan-2-ol salts corresponding to the following general formula:

with X producing pairs of diastereoisomers of different solubilities, or with X producing a conglomerate.

More particularly, the invention is based on the use of a simple and very selective chiral agent which also has the advantage of being easy to prepare and easy to recover on completion of the method. This chiral agent is one of the enantiomers R or S of N-tosyl-leucine.

Hence, when X, in the formula above is one of the enantiomers R or S of N-tosyl-leucine, pairs of diastereoisomers with different solubilities are produced.

According to another aspect of the invention, when X, in the formula above, is trans-cinnamic acid, in certain cases, a conglomerate is produced.

DETAILED DESCRIPTION

The method of the invention is characterized in that it comprises the following steps:
  a) dissolving a compound of formula (I) in racemic form and one of the enantiomers R or S of N-tosyl-leucine, referred to hereafter as TOSLEU, in pure alcohol, in suitable proportions, and then
  b) isolating by any suitable means, the diastereoisomeric salt of the compound of formula (I) in crystallized form.

A suitable means of isolating the diastereoisomeric salt of the compound of formula (I) obtained at step (b) consists of filtration and/or centrifugation. It should be noted that the diastereoisomeric salt of the compound of formula (I) and the splitting agent which is obtained at step (b) is the less soluble one.

Advantageously, at step (a) of the preceding method, about 1 molar equivalent of resolution agent is dissolved for one mole of compound of formula (I) to be split.

Depending on the desired enantiomer of the 1-amino-alkan-2-ol of formula (I), either the R or S enantiomer of the N-tosyl-leucine is used. In the examples of the invention given below, enantiomer S of N-tosyl-leucine has been arbitrarily chosen.

One of the main advantages of the invention is the possibility of allowing very easy recovery of the resolution agent in a strongly acid medium.

The first enantiomer of the compound of formula (I) to be split is easily obtained after step (b) by step (c) defined below:
  c) treatment of the diastereoisomeric salt isolated at step (b) to obtain the first enantiomer of the compound of formula (I) to be split.

The treatment in step (c) consists, for example, of subjecting the diastereoisomeric salt obtained at step (b) to agitation in a basic medium, and then extracting the first enantiomer of the compound of formula (I) to be split with $CH_2Cl_2$.

Other treatments can be considered, notably such as the use of other organic extraction solvents in correlation with the hydrophilic character which is more or less marked for each amino-alcohol. One may use, for example, solvents such as 1,2-dichloroethane, chloroform, ethyl acetate or diethyl ether for 1-amino-3,3-dimethylbutan-2-ol and 1-amino-2-cyclohexylethan-2-ol which are the two amino-alcohols tested below which are the least hydrophilic.

In the case where one wishes to obtain the second enantiomer of the compound of formula (I) to be split, the method of the invention includes step (c') defined below:
  c') treatment of the mother solutions resulting from the isolation of the diastereoisomeric salt from step (b) in order to obtain the second enantiomer of the compound of formula (I) to be split.

It should be noted that the enantiomer recovered following step (c') corresponds to the diastereoisomeric salt of the compound of formula (I) and the splitting agent obtained at step (b) that is the more soluble.

The step (c') treatment consists, for example, of subjecting the mother solutions to evaporation and then treating the residue resulting from the evaporation with a basic solution and extracting the second enantiomer of the compound of formula (I) to be split, for example with $CH_2Cl_2$.

Other treatments can be considered. Among these, one preferred embodiment of the method of the invention suited to certain of the compounds of formula (I) consists of producing the cinnamate of said second enantiomer obtained at step (c'), through the addition of about 1 equivalent of trans-cinnamic acid and then, advantageously, carrying out a recrystallization with ethanol.

The conversion into the cinnamate is particularly useful for recovering and purifying the second enantiomer following step (c'), and is also useful for purifying, if necessary, the first enantiomer after step (c).

Consequently, the method of the invention can comprise, after step (c'), a purification step (d) without loss of the enantiomeric excess by the intermediate creation of the cinnamate of the second enantiomer of the compound of formula (I) to be split.

The inventors have, in addition, observed that the addition of trans-cinnamic acid after step (c'), for certain 1-amino-alkan-2-ol compounds, leads to formation of a conglomerate. The formation of such a conglomerate permits:

the recovery of the enantiomeric excess by the recrystallization methods described in the prior art, and also allows one to significantly increase the yields of this recovery and to achieve levels of enantiomeric purity of the order of 99%.

the application of preferential crystallization techniques.

Among the alternate methods of preferential crystallization known in the prior art, one may mention:

A classic method called SIPC or "Seeded Isothermal Preferential Crystallization" or S3PC which is described in a United Kingdom Patent published under the number GB-A-1197809. This continuous method is based on seeding or preferential nucleation (Eliel, Ernest L., Samuel H. Wilen; Lewis N. Mander. A Wiley-Interscience Publication. John Wiley & Sons Inc.).

An original method called AS3PC which is described in the PCT Patent Application published under the number WO 95/08522. This method is based on the controlled growth of one of the optical enantiomers of the compound to be split and does not make use of either seeding or preferential nucleation.

As a consequence, in the case where step (d) leads to the formation of a conglomerate, the method of the invention comprises a preferential crystallization step (e), advantageously of the AS3PC type.

Figure 1:
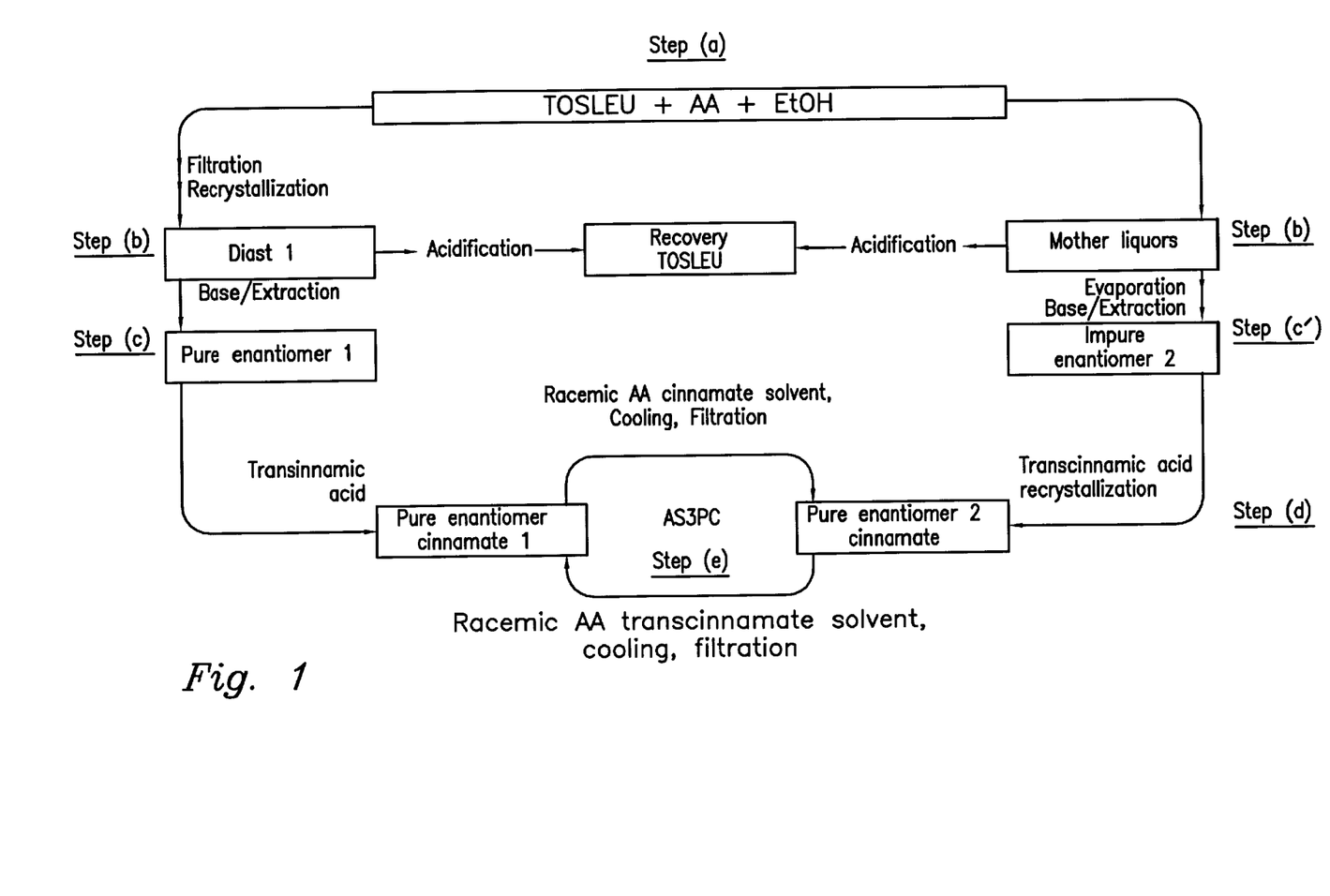
FIG. 1 is a diagram which summarizes the method of the invention, and which indicates the products involved in each of the steps a, b, c, c', d and e.

In FIG. 1 appended, a diagram is shown which summarizes the method of the invention, and which indicates the products involved in each of the steps a, b, c, c', d and e.

In addition the invention relates to the use of one of the enantiomers R or S of N-tosyl-leucine as a splitting agent for 1-amino-alkan-2-ol of general formula:

in which R has the same meaning as previously.

The invention also relates to the use of the trans-cinnamate of an enantiomer of a chiral 1-amino-alkan-2-ol compound for the purification, without loss of the enantiomeric excess, of said enantiomer in a method of splitting chiral 1-amino-alkan-2-ol compounds, the formation of a conglomerate that permits the recovery of the enantiomeric excess by recrystallization methods and more particularly by the alternate methods of preferential crystallization, advantageously AS3PC methods.

More particularly, the invention relates to the application of the method previously described and to its variants to the splitting of the compounds in Table I below.

TABLE I

| Compounds | Formulae | Code |
|---|---|---|
| 1-aminopropan-2-ol | ![structure] | APR |
| 1-aminobutan-2-ol | ![structure] | ABU |
| 1-aminopentan-2-ol | ![structure] | APE |
| 1-amino-3-methylbutan-2-ol | ![structure] | AMB |
| 1-aminohexan-2-ol | ![structure] | AHX |
| 1-amino-4-methylpentan-2-ol | ![structure] | AMP |
| 1-amino-3,3-dimethylbutan-2-ol | ![structure] | ADB |
| 1-aminoheptan-2-ol | ![structure] | AHP |

TABLE I-continued

| Compounds | Formulae | Code |
|---|---|---|
| 1-amino-3-ethylpentan-2-ol | (structure: pentane chain with ethyl branch, OH and NH$_2$ substituents) | AEP |
| 1-amino-2-cyclohexylethan-2-ol | (structure: cyclohexyl group with CH(OH)CH$_2$NH$_2$) | ACE |

In the case of 1-aminopropan-2-ol (APR), more particularly, the application of the method of the invention comprises the following steps:
 a) 1 equivalent of APR and from 0.5 to 1 equivalent of one of the enantiomers R or S of TOSLEU are dissolved with a concentration of the order of 19% by mass in absolute ethanol or any other suitable organic solvent free of water.
 b) After 4 hours agitation, the suspension is filtered so as to recover the pure diastereoisomeric salt (D1), possibly after washing or recrystallization in absolute ethanol.
 c) The salt is treated with a saturated solution of NaOH, then the first enantiomer of the APR is extracted with CH$_2$Cl$_2$. The organic phases are brought together, dried with Na$_2$SO$_4$ and then evaporated so as to obtain the first enantiomer of APR.
 c') The mother liquors from the crystallization in step b) are evaporated and the second enantiomer of APR is obtained as in step (c) but is impure.
 d) Said second enantiomer is purified by producing its cinnamate in stoichiometric fashion in di-isopropyl ether followed by several recrystallizations in ethanol.
 e) Possibly, a portion of the crystals from step (d) is selectively dissolved (AS3PC) in a 24.5% by mass solution of racemic mixture in the form of cinnamate, prepared as in step (d), in ethanol in order to obtain an equilibrium between the saturated solution and the crystals of the cinnamate of the second enantiomer of APR. This suspension is cooled and then filtered so as to obtain a total initial mass of enantiomer greater than the enantiomeric excess with a high optical purity. Still with step (e), the racemic mixture can then be added at a quantity equal to that of the enantiomer obtained in order to isolate, in turn, first one and then the other enantiomer of the APR cinnamate.

In the case of 1-aminobutan-2-ol (ABU), the application of the method of the invention comprises more particularly, the following steps:
 a) 1 equivalent of ABU and from 0.5 to 1 equivalent of one of the enantiomers R or S of TOSLEU are dissolved with a concentration of the order of 7% by mass in absolute ethanol or any other suitable organic solvent free of water.
 b) After 4 hours agitation, the suspension is filtered so as to recover the pure diastereoisomeric salt (D1), possibly after washing or recrystallization in absolute ethanol.
 c) The salt is treated with a saturated solution of NaOH, then the first enantiomer of the ABU is extracted with CH$_2$Cl$_2$. The organic phases are brought together, dried with Na$_2$SO$_4$ and then evaporated so as to obtain the first enantiomer of ABU.
 c') The mother liquors from the crystallization in step b) are evaporated and the second enantiomer of ABU is obtained as in step (c) but is impure.
 d) Said second enantiomer is purified by producing its cinnamate in stoichiometric fashion in di-isopropyl ether followed by several recrystallizations in ethanol.

In the case of 1-aminopentan-2-ol (APE), the application of the method of the invention comprises more particularly, the following steps:
 a) 1 equivalent of APE and from 0.5 to 1 equivalent of one of the enantiomers R or S of TOSLEU are dissolved with a concentration of the order of 15% by mass in absolute ethanol or any other suitable organic solvent free of water.
 b) After 4 hours agitation, the suspension is filtered so as to recover the pure diastereoisomeric salt (D1), possibly after washing or recrystallization in absolute ethanol.
 c) The salt is treated with a saturated solution of NaOH, then the first enantiomer of the APE is extracted with CH$_2$Cl$_2$. The organic phases are brought together, dried with Na$_2$SO$_4$ and then evaporated so as to obtain the first enantiomer of APE.
 c') The mother liquors from the crystallization in step b) are evaporated and the second enantiomer of APE is obtained as in step (c) but is impure.
 d) Said second enantiomer is purified by producing its cinnamate in stoichiometric fashion in di-isopropyl ether followed by several recrystallizations in ethanol.
 e) Possibly, a portion of the crystals from step (d) is selectively dissolved (AS3PC) in a 15.1% by mass solution of racemic mixture in the form of cinnamate, prepared as in step (d), in ethanol in order to obtain an equilibrium between the saturated solution and the crystals of the cinnamate of the second enantiomer of APE. This suspension is cooled and then filtered so as to obtain a total initial mass of enantiomer greater than the enantiomeric excess with a high optical purity. Still with step (e), the racemic mixture can then be added at a quantity equal to that of the enantiomer obtained in order to isolate, in turn, first one and then the other enantiomer of the APE cinnamate.

In the case of 1-amino-3-methylbutan-2-ol (AMB), the application of the method of the invention comprises more particularly, the following steps:
 a) 1 equivalent of AMB and from 0.5 to 1 equivalent of one of the enantiomers R or S of TOSLEU are dissolved with a concentration of the order of 9% by mass in absolute ethanol or any other suitable organic solvent free of water.
 b) After 4 hours agitation, the suspension is filtered so as to recover the pure diastereoisomeric salt (D1), possibly after washing or recrystallization in absolute ethanol.
 c) The salt is treated with a saturated solution of NaOH, then the first enantiomer of the AMB is extracted with CH$_2$Cl$_2$. The organic phases are brought together, dried with Na$_2$SO$_4$ and then evaporated so as to obtain the first enantiomer of AMB.
 c') The mother liquors from the crystallization in step b) are evaporated and the second enantiomer of AMB is obtained as in step (c) but is impure.

d) Said second enantiomer is purified by producing its cinnamate in stoichiometric fashion in di-isopropyl ether followed by several recrystallizations in ethanol.

e) Possibly, a portion of the crystals from step (d) is selectively dissolved (AS3PC) in a 15.0% by mass solution of racemic mixture in the form of cinnamate, prepared as in step (d), in ethanol in order to obtain an equilibrium between the saturated solution and the crystals of the cinnamate of the second enantiomer of AMB. This suspension is cooled and then filtered so as to obtain a total initial mass of enantiomer greater than the enantiomeric excess with a high optical purity. Still with step (e), the racemic mixture can then be added at a quantity equal to that of the enantiomer obtained in order to isolate, in turn, first one and then the other enantiomer of the AMB cinnamate.

In the case of 1-aminohexan-2-ol (AHX), the application of the method of the invention comprises more particularly, the following steps:

a) 1 equivalent of AHX and from 0.5 to 1 equivalent of one of the enantiomers R or S of TOSLEU are dissolved with a concentration of the order of 12% by mass in absolute ethanol or any other suitable organic solvent free of water.

b) After 4 hours agitation, the suspension is filtered so as to recover the pure diastereoisomeric salt (D1), possibly after washing or recrystallization in absolute ethanol.

c) The salt is treated with a saturated solution of NaOH, then the first enantiomer of the AHX is extracted with $CH_2Cl_2$. The organic phases are brought together, dried with $Na_2SO_4$ and then evaporated so as to obtain the first enantiomer of AHX.

c') The mother liquors from the crystallization in step b) are evaporated and the second enantiomer of AHX is obtained as in step (c) but is impure.

d) Said second enantiomer is purified by producing its cinnamate in stoichiometric fashion in di-isopropyl ether followed by several recrystallizations in ethanol.

e) Possibly, a portion of the crystals from step (d) is selectively dissolved (AS3PC) in a 15.0% by mass solution of racemic mixture in the form of cinnamate, prepared as in step (d), in ethanol in order to obtain an equilibrium between the saturated solution and the crystals of the cinnamate of the second enantiomer of AHX. This suspension is cooled and then filtered so as to obtain a total initial mass of enantiomer greater than the enantiomeric excess with a high optical purity. Still with step (e), the racemic mixture can then be added at a quantity equal to that of the enantiomer obtained in order to isolate, in turn, first one and then the other enantiomer of the AHX cinnamate.

In the case of 1-amino-4-methylpentan-2-ol (AMP), the application of the method of the invention comprises more particularly, the following steps:

a) 1 equivalent of AMP and from 0.5 to 1 equivalent of one of the enantiomers R or S of TOSLEU are dissolved with a concentration of the order of 9% by mass in absolute ethanol or any other suitable organic solvent free of water.

b) After 4 hours agitation, the suspension is filtered so as to recover the pure diastereoisomeric salt (D1), possibly after washing or recrystallization in absolute ethanol.

c) The salt is treated with a saturated solution of NaOH, then the first enantiomer of the AMP is extracted with $CH_2Cl_2$. The organic phases are brought together, dried with $Na_2SO_4$ and then evaporated so as to obtain the first enantiomer of AMP.

c') The mother liquors from the crystallization in step b) are evaporated and the second enantiomer of AMP is obtained as in step (c) but is impure.

d) Said second enantiomer is purified by producing its cinnamate in stoichiometric fashion in di-isopropyl ether followed by several recrystallizations in ethanol.

e) Possibly, a portion of the crystals from step (d) is selectively dissolved (AS3PC) in a 15.1% by mass solution of racemic mixture in the form of cinnamate, prepared as in step (d), in ethanol in order to obtain an equilibrium between the saturated solution and the crystals of the cinnamate of the second enantiomer of AMP. This suspension is cooled and then filtered so as to obtain a total initial mass of enantiomer greater than the enantiomeric excess with a high optical purity. Still with step (e), the racemic mixture can then be added at a quantity equal to that of the enantiomer obtained in order to isolate, in turn, first one and then the other enantiomer of the AMP cinnamate.

In the case of 1-amino-3,3-dimethylbutan-2-ol (ADB), the application of the method of the invention comprises more particularly, the following steps:

a) 1 equivalent of ADB and from 0.5 to 1 equivalent of one of the enantiomers R or S of TOSLEU are dissolved with a concentration of the order of 9% by mass in absolute ethanol or any other suitable organic solvent free of water.

b) After 4 hours agitation, the suspension is filtered so as to recover the pure diastereoisomeric salt (D1), possibly after washing or recrystallization in absolute ethanol.

c) The salt is treated with a saturated solution of NaOH, then the first enantiomer of the ADB is extracted with $CH_2Cl_2$. The organic phases are brought together, dried with $Na_2SO_4$ and then evaporated so as to obtain the first enantiomer of ADB.

c') The mother liquors from the crystallization in a step b) are evaporated and the second enantiomer of ADB is obtained as in step (c) but is impure. The purification could be carried out with the other TOSLEU enantiomer.

In the case of 1-aminoheptan-2-ol (AHP), the application of the method of the invention comprises more particularly, the following steps:

a) 1 equivalent of AHP and from 0.5 to 1 equivalent of one of the enantiomers R or S of TOSLEU are dissolved with a concentration of the order of 9% by mass in absolute ethanol or any other suitable organic solvent free of water.

b) After 4 hours agitation, the suspension is filtered so as to recover the pure diastereoisomeric salt (D1), possibly after washing or recrystallization in absolute ethanol.

c) The salt is treated with a saturated solution of NaOH, then the first enantiomer of the AHP is extracted with $CH_2Cl_2$. The organic phases are brought together, dried with $Na_2SO_4$ and then evaporated so as to obtain the first enantiomer of AHP.

c') The mother liquors from the crystallization in step b) are evaporated and the second enantiomer of AHP is obtained as in step (c) but is impure. The purification could be carried out with the other TOSLEU enantiomer.

In the case of 1-amino-3-ethylpentan-2-ol (AEP), the application of the method of the invention comprises more particularly, the following steps:

a) 1 equivalent of AEP and from 0.5 to 1 equivalent of one of the enantiomers R or S of TOSLEU are dissolved with a concentration of the order of 2% by mass in absolute ethanol or any other suitable organic solvent free of water.

b) After 4 hours agitation, the suspension is filtered so as to recover the pure diastereoisomeric salt (D1), possibly after washing or recrystallization in absolute ethanol.

c) The salt is treated with a saturated solution of NaOH, then the first enantiomer of the AEP is extracted with $CH_2Cl_2$. The organic phases are brought together, dried with $Na_2SO_4$ and then evaporated so as to obtain the first enantiomer of AEP.

c') The mother liquors from the crystallization in step b) are evaporated and the second enantiomer of AEP is obtained as in step (c) but is impure. The purification could be carried out with the other TOSLEU enantiomer.

In the case of 1-amino-2-cyclohexylethan-2-ol (ACE), the application of the method of the invention comprises more particularly, the following steps:

a) 1 equivalent of ACE and from 0.5 to 1 equivalent of one of the enantiomers R or S of TOSLEU are dissolved with a concentration of the order of 4% by mass in absolute ethanol or any other suitable organic solvent free of water.

b) After 4 hours agitation, the suspension is filtered so as to recover the pure diastereoisomeric salt (D1), possibly after washing or recrystallization in absolute ethanol.

c) The salt is treated with a saturated solution of NaOH, then the first enantiomer of the ACE is extracted with $CH_2Cl_2$. The organic phases are brought together, dried with $Na_2SO_4$ and then evaporated so as to obtain the first enantiomer of ACE.

c') The mother liquors from the crystallization in step b) are evaporated and the second enantiomer of ACE is obtained as in step (c) but is impure.

d) Said second enantiomer is purified by producing its cinnamate in stoichiometric fashion in di-isopropyl ether followed by several recrystallizations in ethanol.

e) Possibly, a portion of the crystals from step (d) is selectively dissolved (AS3PC) in an 8.2% by mass solution of racemic mixture in the form of cinnamate, prepared as in step (d), in ethanol in order to obtain an equilibrium between the saturated solution and the crystals of the cinnamate of the second enantiomer of ACE. This suspension is cooled and then filtered so as to obtain a total initial mass of enantiomer greater than the enantiomeric excess with a high optical purity. Still with step (e), the racemic mixture can then be added at a quantity equal to that of the enantiomer obtained in order to isolate, in turn, first one and then the other enantiomer of the ACE cinnamate.

The preferential crystallization (AS3PC) in the steps (e) above could be replaced by a less advantageous traditional crystallization (SIPC).

Other advantages and characteristics of the invention will become apparent on reading the examples which follow which are non-limitative and relate to the preparation of 1-amino-alkan-2-ols (±) to be split and of N-tosyl-leucine, as well as the implementation of the method of the invention with a preferential crystallization AS3PC step.

I—Preparation of the 1-amino-alkan-2-ols (±)

The amino-alcohols of Table I were prepared.

The preparations were carried out using the Henry reaction (19) in which the yield is between 65 and 85%, followed by catalytic hydrogenation, under the following conditions:

Pd/C in dry alcohol $P(H_2) \cong 2$ atm.

The yields were between 80% and 85%. All the amino-alcohols (+) and (±) have a melting point between 5° C. and 30° C. with the exception of ADB (Racemate: M.pt=63.8° C.; ΔH=180 J/g.
Enantiomer: M.pt=43.3° C.; ΔH=101 J/g)

ACE (Racemate: M.pt=85.7° C.; ΔH=178 J/g.
Enantiomer: M.pt=85.0° C.; ΔH=174 J/g).

Resolution by the bias of the diastereoisomeric salts of the compounds in Table I was carried out according to the invention, using the same resolution agent, (S)N-tosyl-leucine, hereafter called (S)TOSLEU.

II—Syntheses of (S)TOSLEU

In a reflux flask, 13.25 g of (S)leucine (0.1 mol; Aldrich 99%), 29.1 g of $K_2CO_3$ and 300 cc of $H_2O$ were mixed and heated to 65° C. After dissolution under constant agitation, 21 g of tosyl chloride is added (0.11 mol. recrystallized in accordance with the Pelletier method (20)). After 2 hours, 300 cc of cold water is poured in. When a temperature of 20° C. is reached, the tosyl chloride which has not reacted is extracted with 2×50 cc of $CH_2Cl_2$. The aqueous solution is then cooled to 0° C., then acidified with a concentrated solution of HCl in excess with vigorous agitation. The greater part of (S)TOSLEU is recovered by filtration and the part remaining in aqueous solution is extracted with 2×50 cc of $CH_2Cl_2$. The organic phases and the solid are collected and dried with $Na_2SO_4$. The solvent is removed by evaporation and the product crystallizes spontaneously at 0° C. The distinctive feature of the purification method consists in vigorously stirring the crystals in 100 cc of $H_2O$ for 24 hours (21, 22). The solution is then cooled to 6° C. and the purified solid is filtered and gives 20.8 g of (S)TOSLEU, being a yield of 73%.

III—General Procedure for the Resolution of (±) 1-amino-alkan-2-ols Using (S)TOSLEU as Resolving Agent 1) Preparation of the No. 1 Enantiomer from the Less Soluble Diastereoisomeric Salt with (S)TOSLEU A quantity of $X_2$ moles (column 2 of Table II below) of amino-alcohol and one equivalent of (S)TOSLEU are dissolved by heating in $X_3$ cc of dry ethanol (column 3 of Table II below). The mixture is left 4 hours at 25° C. under constant agitation. The crystallized phase is filtered and dried to provide $X_4$ grams of the raw diastereoisomeric salt (column 4 of Table II below) with an optical purity of $X_5$% (column 5 of Table II below).

Recrystallization with ethanol gives a pure salt the characteristics of which are given in table II below where the yields are shown in column 6. The theoretical yield indicated in this column 6 is the optical yield.

The pure salt is stirred for 15 minutes in an aqueous solution of NaOH in excess and extracted with $CH_2Cl_2$. The organic fractions collected are dried by using $Na_2SO_4$ and the solvent is removed by evaporation under vacuum to give the enantiomer whose characteristics are summarized in Table II below where the yields $X_7$ are shown in column 7.

| Code | 2 Mass (g) of amino- alcohol (No. of eq. x $10^3$) | 3 EtOH (cc) | 4 Mass (g) salt 1 | 5 Optical purity (%) | 6 Yield (%) of pure salt 1 Theo. (exp.) | 7 O.P. (%) of pure base 1 $(\alpha)_{436}$/MeOH c = 1 20° C. | 8 Yield (%) of cinna- mate enant- iomer 2 | 9 (%) of cinna- mate enant- iomer 2 | 10 Yield (%) of pure base 2 |
|---|---|---|---|---|---|---|---|---|---|
| APR | 0.390 (5.2) | 8.3 | 0.87 | 64 | 59.6 (42) | 26 (+44.1) | 57 | 31 | 20 |
| ABU | 0.305 (3.4) | 16.6 | 0.61 | 76 | 72.2 (63) | 51 (+13.3) | 67 | 43 | 31 |
| APE | 1.040 (10.0) | 23.2 | 1.22 | >99 | 62.5 (62) | 49 (+11.4) | 46 | 38 | 27 |
| AMB | 1.124 (10.9) | 46.7 | 1.87 | 67 | 59.2 (52) | 42 (+36.6) | 53 | 31 | 21 |
| AHX | 1.494 (12.7) | 40.4 | 1.84 | 86 | 61.6 (55) | 48 (−6.1) | 47 | 44 | 37 |
| AMP | 1.024 (8.7) | 24.4 | 1.22 | 95 | 65.8 (55) | 55 (−26.0) | 51 | 55 | 53 |
| ADB | 1.000 (8.5) | 34.2 | 1.14 | 96 | 63.4 (60) | 57 (+64.4) | 49 | — | — |
| AHP | 1.000 (7.6) | 26.3 | 1.21 | 89 | 67.8 (60) | 54 (−8.8) | 57 | — | — |
| AEP | 1.484 (11.3) | 193.6 | 1.71 | >99 | 72.6 (72) | 70 (+15.1) | 57 | — | — |
| ACE | 0.547 (3.8) | 45.3 | 0.57 | 90 | 62.5 (57) | 57 (+20.8) | 48 | 54 | 54 |

In Table II above;

Columns 2 and 3 show the procedure for the resolution of the (±) 1-amino-alkan-2-ol using (S)TOSLEU;

Columns 4 to 7 show the results for enantiomer 1,

Columns 8 to 10 show the results for enantiomer 2.

Table III below gives the properties of the less soluble salt of (S)TOSLEU with enantiomer No. 1 of the 1-amino-alkan-2-ol.

Apart from AMB, ADB and AEP, all the other salts show a well characterized phenomenon of polymorphism. Furthermore, by its temperature (column 3) and its enthalpy (column 4) another polymorphism phenomenon just before melting is detected for APR and ACE.

TABLE III

| 2 Code | 2 F.W. (amine) | 3 T (trans) °C. | 4 ΔH (trans) J/g | 5 T (fusion) °C. | 6 ΔH (fusion) J/g | 7 ($\alpha$) 20° C./ λ = 436 nm MeOH/c = 1 g/100 ml/ |
|---|---|---|---|---|---|---|
| APR | 75.11 | 138.8 | 12 | 166.6 | 61 | +77.0 |
| ABU | 89.14 | 136.8 | 8 | 187.8 | 87 | +66.2 |
| APE | 103.16 | 45.8 | 8 | 180.0 | 92 | +57.9 |
| AMB | 103.16 | — | — | 205.4 | 90 | +69.8 |
| AHX | 117.19 | 41.0 | 8 | 181.4 | 94 | +62.0 |
| AMP | 117.19 | 60.1 | 11 | 192.1 | 79 | +51.6 |
| ADB | 117.19 | — | — | 198.4 | 83 | +76.8 |
| AHP | 131.22 | 142.5 | 3 | 172.5 | 87 | +56.1 |
| AEP | 131.22 | — | — | 202.5 | 91 | +64.7 |
| ACE | 131.22 | 60.3 | 17 | 211.5 | 96 | +64.3 |

2) Recovery of the No. 2 enantiomer corresponding to the more soluble diastereoisomeric salt with (S)TOSLEU The mother liquor resulting from the filtration product $X_4$ is evaporated and the residue is treated with an excess of aqueous NaOH solution. The amino-alcohol is extracted with $CH_2Cl_2$ and then dried. One equivalent of trans-cinnamic acid is added to the dry solution. The solvent is evaporated and the crystals that remain are washed in 5 cc of di-isopropyl ether. The cinnamate with optical purity $X_8$ (column 8 in Table II above) is filtered and recrystallized with ethanol. The final yields of pure cinnamate $X_9$% and of amino-alcohol $X_{10}$ are given respectively in columns 9 and 10 of Table II above.

3) Adaptation of the Method

The method described above has been adapted for compounds APR and ABU in the following way.

The salt is dissolved and agitated in an excess of aqueous NaOH solution and then the solution is saturated with NaOH. A large quantity of $CH_2Cl_2$ is added with vigorous agitation. The two phase mixture is agitated for 24 hours and filtered under vacuum. The organic phase is then dried with $Na_2SO_4$.

IV—Resolution By Preferential Crystallization

Seven of the ten trans-cinnamates prepared in the preceding examples crystallize in the form of a conglomerate. The physical properties of the enantiomer and of the racemic mixture are summarized in Table IV below. In Table IV: "*" signifies that polymorphism is observed just before melting and "**" signifies that a ok metastable racemate is observed.

TABLE IV

| Code | M. Pt. (° C.) Enant. | ΔHf (J/g) Enant. | M. Pt. (° C.) O. P. = 0 | ΔHf (J/g) O. P. = 0 | (α) 20 (°) λ = 436 c = 1 MeOH | Type of racemic mixture |
|---|---|---|---|---|---|---|
| APR | 129.9* | 150 | 105.3* | 115 | 34.8 | conglomerate |
| ABU | 147.5* | 160 | 124.5* | 160 | 20.1 | conglomerate (**) |
| APE | 158.6* | 175 | 137.5* | 160 | 13.8 | conglomerate |
| AMB | 155.0* | 121 | 135.2* | 119 | 29.8 | conglomerate (**) |
| AHX | 154.0* | 162 | 132.7* | 143 | 12.4 | conglomerate (**) |
| AMP | 160.8 | 158 | 139.8* | 149 | 16.0 (c = 4) | conglomerate |
| ADB | — | — | — | — | — | racemate |
| AHP | — | — | — | — | — | racemate |
| AEP | — | — | — | — | — | racemate |
| racemic ACE | 181.1* | 132 | 163.8 | 23.4 | 23.4 | conglomerate |

As no solid solution between the enantiomers was detected, the purification of the following pairs was able to be carried out with high enantiomeric purity (O.P.>99%): APR, ABU, APE, AMB, AHX, AMP and ACE. The cinnamates are prepared in di-isopropyl ether and the recrystallizations are carried out in a mixture of ethanol and ethyl acetate (50/50 vol. %).

The preferential crystallizations were carried out using the AS3PC method described in the PCT Patent Application published under the No. WO 95/08522, the disclosure from which is incorporated here through a reference. This method is particularly advantageous since it does not necessitate any seeding, provides good reproducibility of results and gives high optical purity. The examples below describe the implementation of the AS3PC method and the results obtained from it with the compounds mentioned previously.

1) Resolution of the (±) APR Trans-cinnamate
a) Properties of the compound

|  | Enantiomer | Racemic mixture |
|---|---|---|
| Melting Point (° C.) | 129.9 | 105.3 |
| Enthalpy of fusion (J/g) | 150 | 115 |

Specific optical property (Temperature: 20° C.; mass of enantiomer: 1 g dissolved in 100 ml of methanol):

| λ (nm) | 589 | 578 | 546 | 436 | 365 |
|---|---|---|---|---|---|
| (α) 20 (°) | — | 18.8 | 21.1 | 34.8 | 52.6 | b) Resolution by the AS3PC method
Thermodynamic Data
Solubility of the racemic mixture in ethanol with respect to temperature:

| T (° C.) | 5.6 | 10.6 | 15.6 | 20.5 | 25.5 |
|---|---|---|---|---|---|
| s (Mass %) | 14.9 | 16.6 | 19.2 | 22.6 | 27.6 |

Solubility of the enantiomer at: 15.6° C., s=8.9% (mass); ratio α=2.15 at 15.6° C.
Co-ordinates of the point L: 24.5% at 22.7° C.

$T_{HOMO}$ as a function of the enantiomeric excess (the ratio (mass of racemic mixture/mass of solvent+mass of racemic mixture) is kept constant).

| e. e. (%) | 0 | 2 | 4 | 6.5 |
|---|---|---|---|---|
| $T_{HOMO}$ (° C.) | 22.7 | 23.6 | 24.7 | 26.0 |

Kinetic Data
$T_B=24.4°$ C.
$T_F=15.6°$ C.
T=f(t): temperature as a function of time

| T (° C.) | 24.4 | 22.5 | 20.7 | 18.9 | 17.1 | 15.6 | 15.6 |
|---|---|---|---|---|---|---|---|
| time (min) | 0 | 10 | 20 | 30 | 40 | 50 | 55 |

The duration of supersaturation of the homogeneous solution L under the effect of the cooling law defined above: 90 minutes with a speed of agitation of 300 rpm.
Duration of the crystallization: 55 minutes
Initial Conditions
Enantiomeric excess: 6.5%.

| Mass of ± (g) | Mass of pure ( ) (g) | Mass of solvent (g) |
|---|---|---|
| 28.37 | 1.97 | 87.44 |

Duration of the plateau at $T_B$=50 minutes
Speed of agitation: 200 rpm at the start and 300 rpm at the finish of the crystallization.
Results

| No. | Mass of pure enantiomer (g) | Optical purity (%) | Compensation of solution L (g) |
|---|---|---|---|
| 1 | 3.95 | 88.3 | 3.22 |
| 2 | 3.76 | 84.5 | 3.05 |
| 3 | 3.74 | 83.0 | 3.37 |

-continued

| No. | Mass of pure enantiomer (g) | Optical purity (%) | Compensation of solution L (g) |
|---|---|---|---|
| 4 | 4.05 | 84.8 | 2.53 |
| 5 | 3.69 | 90.7 | 1.22 |
| 6 | 3.69 | 86.6 | 2.89 |
| 7 | 3.51 | 85.7 | 2.03 |
| 8 | 3.65 | 87.2 | — |

Mean mass of the pure enantiomer: 3.75 g.
Mean e.e.: 6.2% corresponding to 1.88 g of antipode
Mean optical purity of the raw crystals: 86% with neither recrystallization nor washing.

2) Resolution of the (±) APE Trans-cinnamate
a) Properties of the compound

|  | Enantiomer | Racemic mixture |
|---|---|---|
| Melting Point (° C.) | 158.6 | 137.5 |
| Enthalpy of fusion (J/g) | 175 | 160 |

Specific optical property (Temperature 20° C.; mass of enantiomer: 1 g dissolved in 100 ml of methanol):

| λ (nm) | 589 | 578 | 546 | 436 | 365 |
|---|---|---|---|---|---|
| (α) 20 (°) | 6.8 | 7.1 | 8.3 | 13.8 | 21.2 | b) Resolution by the AS3PC method
Thermodynamic Data
Solubility of the racemic mixture in methanol with respect to temperature:

| T (° C.) | 10.7 | 12.8 | 15.3 | 16.1 | 26.4 | 35.2 |
|---|---|---|---|---|---|---|
| s (Mass %) | 13.7 | 14.0 | 14.8 | 15.1 | 20.0 | 24.9 |

Solubility of the enantiomer at: 16.1° C., s=9.2% mass); ratio α=1.64 at 16.1° C.
Co-ordinates of the point L: 15.1% at 16.1° C.
$T_{HOMO}$ as a function of the enantiomeric excess (the ratio (mass of racemic mixture/mass of solvent+mass of racemic mixture) is kept constant).

| e. e. (%) | 0 | 2.0 | 4.7 |
|---|---|---|---|
| $T_{HOMO}$ (° C.) | 16.1 | 17.3 | 18.8 |

Kinetic Data
$T_B$=17.5° C.
$T_F$=10.7° C.
T=f(t): temperature as a function of time

| T (° C.) | 17.5 | 12.9 | 11.2 | 11.2 | 10.7 |
|---|---|---|---|---|---|
| time (min) | 0 | 13 | 20 | 50 | 60 |

The duration of supersaturation of the homogeneous solution L under the effect of the cooling law defined above: 80 minutes with a speed of agitation of 150 rpm.
Duration of the crystallization: 60 minutes Initial Conditions
Enantiomeric excess: 4.3%.

| Mass of (±) (g) | Mass of pure ( ) (g) | Mass of solvent (g) |
|---|---|---|
| 4.238 | 0.190 | 23.86 |

Duration of the plateau at $T_B$=50 minutes
Speed of agitation: 150 rpm at the start and 180 rpm at the finish of the crystallization.
Results

| No. | Mass of pure enantiomer (g) | Optical purity (%) | Compensation of solution L (g) |
|---|---|---|---|
| 1 | 0.417 | 90.5 | 1.1 |
| 2 | 0.447 | 90.9 | 1.3 |
| 3 | 0.468 | 93.0 | 0.80 |
| 4 | 0.483 | 96.7 | 0.71 |
| 5 | 0.471 | 88.3 |  |

Mean mass of the pure enantiomer: 0.474 g for experiments 3 to 5
Mean e.e.: 5.3% corresponding to 0.237 g of antipode
Mean optical purity of the raw crystals: 91.8% with neither recrystallization nor washing.

3) Resolution of the AMB(±) Trans-cinnamate
a) Properties of the compound

|  | Enantiomer | Racemic mixture |
|---|---|---|
| Melting Point (° C.) | 155.0 | 135.2 |
| Enthalpy of fusion (J/g) | 121 | 119 |

Specific optical property (Temperature: 20° C.; mass of enantiomer: 1 g dissolved in 100 ml of methanol):

| λ (nm) | 589 | 578 | 546 | 436 | 365 |
|---|---|---|---|---|---|
| (α) 20 (°) | 15.1 | 16.0 | 18.0 | 29.8 | 44.9 | b) Resolution by the AS3PC method
Thermodynamic Data
Solubility of the racemic mixture in methanol with respect to temperature:

| T (° C.) | 5.3 | 10.3 | 15.3 | 19.3 | 22.8 | 23.2 | 27.6 |
|---|---|---|---|---|---|---|---|
| s (Mass %) racemate | 20.3 | 22.1 | 25.8 | — | — | — | — |
| s (Mass %) conglomerate | 7.7 | 8.8 | 10.0 | 11.3 | 12.7 | 13.0 | 15.0 |

Solubility of the enantiomer at: 27.6° C., s=7.75% (mass); ratio α=1.93 at 27.6° C.
Co-ordinates of the point L: 15.0% at 27.6° C.
$T_{HOMO}$ as a function of the enantiomeric excess (the ratio (mass of racemic mixture/mass of solvent+mass of racemic mixture) is kept constant).

| e. e. (%) | 0 | 2.0 | 4.0 | 6.0 |
|---|---|---|---|---|
| $T_{HOMO}$ (° C.) | 27.6 | 28.7 | 29.8 | 30.9 |

Kinetic Data $T_B$=28.6° C.

$T_F$=23.2° C.

T=f(t): temperature as a function of time

| T (° C.) | 28.6 | 27.2 | 27.2 | 25.2 | 25.2 | 23.2 | 23.2 |
|---|---|---|---|---|---|---|---|
| time (min) | 0 | 6 | 16 | 22 | 41 | 51 | 69 |

The duration of supersaturation of the homogeneous solution L under the effect of the cooling law defined above: 75 minutes with a speed of agitation of 180 rpm.

Duration of the crystallization: 69 minutes

Initial Conditions

Enantiomeric excess: 3.52%.

| Mass of (±) (g) | Mass of pure ( ) (g) | Mass of solvent (g) |
|---|---|---|
| 7.119 | 0.260 | 40.335 |

Duration of the plateau at $T_B$=45 minutes

Speed of agitation: 100 rpm at the start and 120 rpm at the finish of the crystallization.

Results

| No. | Mass of pure enantiomer (g) | Optical purity (%) | Compensation of solution L (g) |
|---|---|---|---|
| 1 | 0.562 | 83 | 1.10 |
| 2 | 0.520 | 85 | — |

Mean mass of the pure enantiomer 0.541 g.

Mean e.e. 3.65% corresponding to 0.270 g of antipode

Mean optical purity of the raw crystals: 84% with neither recrystallization nor washing.

4) Resolution of the (±) AHX Trans-cinnamate a) Properties of the compound

| | Enantiomer | Racemic mixture |
|---|---|---|
| Melting Point (° C.) | 154.0 | 132.7 |
| Enthalpy of fusion (J/g) | 143 | 162 |

Specific optical property (Temperature: 20° C.; mass of enantiomer: 1 g dissolved in 100 ml of methanol):

| λ (nm) | 546 | 436 | 365 |
|---|---|---|---|
| (α) 20 (°) | 7.2 | 12.4 | 19.1 | b) Resolution by the AS3PC method

Thermodynamic Data

Solubility of the racemic mixture in methanol with respect to temperature:

| T (° C.) | 13.1 | 17.2 | 18.7 | 21.5 |
|---|---|---|---|---|
| s (Mass %) | 11.8 | 13.2 | 13.7 | 15.0 |

Solubility of the enantiomer at: 21.5° C., s=9.5% (mass); ratio α=1.58 at 21.5° C.

Co-ordinates of the point L: 15.0% at 21.5° C.

$T_{HOMO}$ as a function of the enantiomeric excess (the ratio (mass of racemic mixture/mass of solvent+mass of racemic mixture) is kept constant).

| e. e. (%) | 0 | 2.0 | 4.7 |
|---|---|---|---|
| $T_{HOMO}$ (° C.) | 21.5 | 22.7 | 24.0 |

Kinetic Data $T_B$=22.7° C.

$T_F$=18.7° C.

T=f(t): temperature as a function of time

| T (° C.) | 22.7 | 19.1 | 18.7 | 18.7 |
|---|---|---|---|---|
| time (min) | 0 | 7 | 14 | 20 |

The duration of supersaturation of the homogeneous solution L under the effect of the cooling law defined above: 40 minutes with a speed of agitation of 150 rpm.

Duration of the crystallization: 20 minutes

Initial Conditions

Enantiomeric excess: 2.6%.

| Mass of (±) (g) | Mass of pure ( ) (g) | Mass of solvent (g) |
|---|---|---|
| 4.238 | 0.110 | 24.0 |

Duration of the plateau at $T_B$=30 minutes

Speed of agitation: 100 rpm at the start and 120 rpm at the finish of the crystallization.

Results

| No. | Mass of pure enantiomer (g) | Optical purity (%) | Compensation of solution L (g) |
|---|---|---|---|
| 1 | 0.218 | 95 | 0.65 |
| 2 | 0.212 | 92 | — |

Mean mass of the pure enantiomer 0.215 g.

Mean e.e.: 2.5% corresponding to 0.107 g of antipode

Mean optical purity of the raw crystals: 93.5% with neither recrystallization nor washing.

5) Resolution of the (±) AMP Trans-cinnamate a) Properties of the compound

| | Enantiomer | Racemic mixture |
|---|---|---|
| Melting Point (° C.) | 160.8 | 139.8 |
| Enthalpy of fusion (J/g) | 158 | 149 |

Specific optical property (Temperature: 20° C.; mass of enantiomer: 4 g dissolved in 100 ml of methanol):

| λ (nm) | 436 | 365 |
|---|---|---|
| (α) 20 (°) | 16.0 | 26.9 | b) Resolution by the AS3PC method

Thermodynamic Data

Solubility of the racemic mixture in methanol with respect to temperature:

| T (° C.) | −15 | 0.5 | 6.4 | 13.1 | 20.2 |
|---|---|---|---|---|---|
| s (Mass %) | 10.5 | 11.5 | 12.9 | 15.1 | 18.3 |

Solubility of the enantiomer at: 13.1° C., s=9.4% (mass); ratio α=1.61 at 13.1° C.

Co-ordinates of the point L: 15.1% at 13.1° C.

$T_{HOMO}$ as a function of the enantiomeric excess (the ratio (mass of racemic mixture/mass of solvent+mass of racemic mixture) is kept constant).

| e. e. (%) | 0 | 2.0 | 4.0 |
|---|---|---|---|
| $T_{HOMO}$ (° C.) | 13.1 | 14.4 | 15.4 |

Kinetic Data $T_B$=14.5° C.

$T_F$=6.4° C.

T=f(t): temperature as a function of time

| T (° C.) | 14.5 | 9.5 | 6.4 | 6.4 |
|---|---|---|---|---|
| time (min) | 0 | 20 | 30 | 48 |

The duration of supersaturation of the homogeneous solution L under the effect of the cooling law defined above: 60 minutes with a speed of agitation of 120 rpm.

Duration of the crystallization: 48 minutes

Initial Conditions

Enantiomeric excess: 3.9%.

| Mass of (±) (g) | Mass of pure ( ) (g) | Mass of solvent (g) |
|---|---|---|
| 4.238 | 0.174 | 23.89 |

Duration of the plateau at $T_B$=30 minutes

Speed of agitation: 100 rpm at the start and 120 rpm at the finish of the crystallization.

Results

| No. | Mass of pure enantiomer (g) | Optical purity (%) | Compensation of solution L (g) |
|---|---|---|---|
| 1 | 0.380 | 95 | 0.43 |
| 2 | 0.463 | 96 | 1.20 |
| 3 | 0.483 | 95 | 0.65 |
| 4 | 0.493 | 94 | 1.00 |
| 5 | 0.473 | 96 | 0.47 |
| 6 | 0.504 | 95 | 0.99 |
| 7 | 0.517 | 96 | 0.65 |
| 8 | 0.520 | 91 | 0.82 |
| 9 | 0.520 | 95 | 0.56 |

Mean mass of the pure enantiomer for experiments 6 to 9: 0.515 g.

Mean e.e.: 5.7% corresponding to 0.257 g of antipode

Mean optical purity of the raw crystals: 94% with neither recrystallization nor washing.

6) Resolution of the (±) ACE Trans-cinnamate a) Properties of the compound

|  | Enantiomer | Racemic mixture |
|---|---|---|
| Melting Point (° C.) | 181.1 | 163.8 |
| Enthalpy of fusion (J/g) | 132 | 99 |

Specific optical property (Temperature: 20° C.; mass of enantiomer: 1 g dissolved in 100 ml of methanol):

| λ (nm) | 578 | 546 | 436 | 365 |
|---|---|---|---|---|
| (α) 20 (°) | 12.7 | 14.4 | 23.4 | 34.8 | b) Resolution by the AS3PC method

Thermodynamic Data

Solubility of the racemic mixture in ethanol with respect to temperature:

| T (° C.) | 15.8 | 18.5 | 22.7 | 28.5 |
|---|---|---|---|---|
| s (Mass %) | 7.4 | 7.5 | 8.2 | 9.6 |

Solubility of the enantiomer at: 22.7° C., s=4.95% (mass); ratio α=1.66 at 22.7° C.

Co-ordinates of the point L: 8.2% at 22.7° C.

$T_{HOMO}$ as a function of the enantiomeric excess (the ratio (mass of racemic mixture/mass of solvent+mass of racemic mixture) is kept constant).

| e. e. (%) | 0 | 3.5 | 4.8 |
|---|---|---|---|
| $T_{HOMO}$ (° C.) | 22.7 | 24.9 | 25.7 |

Kinetic Data $T_B$=24.8° C.

$T_F$=15.8° C.

T=f(t): temperature as a function of time

| T (° C.) | 24.8 | 23.3 | 21.8 | 20.3 | 18.8 | 17.3 | 15.8 | 15.8 |
|---|---|---|---|---|---|---|---|---|
| time (min) | 0 | 10 | 20 | 30 | 40 | 50 | 60 | 70 |

The duration of supersaturation of the homogeneous solution L under the effect of the cooling law defined above: 80 minutes with a speed of agitation of 300 rpm.

Duration of the crystallization: 70 minutes
Initial Conditions
Enantiomeric excess: 3.45%.

| Mass of (±) (g) | Mass of pure ( ) (g) | Mass of solvent (g) |
| --- | --- | --- |
| 2.964 | 0.106 | 33.307 |

Duration of the plateau at $T_B$=60 minutes
Speed of agitation: 300 rpm at the start and 300 rpm at the finish of the crystallization.
Results

| No. | Mass of pure enantiomer (g) | Optical purity (%) | Compensation of solution L (g) |
| --- | --- | --- | --- |
| 1 | 0.324 | 93 | 1.50 |
| 2 | 0.299 | 93 | |

Mean mass of the pure enantiomer: 0.312 g.
Mean e.e.: 5.0% corresponding to 0.156 g of antipode
Mean optical purity of the raw crystals: 93% with neither recrystallization nor washing.

V—Control of the Enantiomeric Purity

The enantiomeric purity was determined by polarimetry and by chiral chromatography in the gaseous phase. This work allowed one to verify that the diastereoisomeric salts and the cinnamates obtained by recrystallization are indeed of high purity.

The Example of AMP

The analyses were carried out on a column made in the laboratory with perpentylated β-cyclodextrin. The 1-amino-4-methylpentan-2-ol (AMP) was mono-trifluoroacetylated in accordance with the following method: With agitation at ambient temperature, an excess of trifluoroacetic anhydride is added to 1 equivalent of amino-alcohol in dichloromethane. After a few minutes, an excess of methanol is added and then the agitation is allowed to continue for 24 hours. The solution is evaporated and leaves a yellowish oil. This is diluted in methanol to be injected into the column.

The results for the enantiomeric excess obtained for AMP are summarized in the table below:

| | e. e; (%) arising from the less soluble salt with (S) TOSLEU * | e. e; arising from the cinnamate of the more soluble base with (S) TOSLEU ** |
| --- | --- | --- |
| AMP | 99.3 ± 0.3 | 99.7 ± 0.3 |

* (−) 1-amino-4-methylpentan-2-ol under measurement conditions (α) 20° C./λ = 436 nm (c = 1/MeOH)
** (+) 1-amino-4-methylpentan-2-ol arising from the cinnamate (−) under the preceding measurement conditions.

VI—Preparation of the Less Soluble Diastereoisomeric Salt of 1-amino-2-propanol

1) First Step 25.64 g (1 eq.) of aminopropanol (Acros 95%) previously distilled in the presence of $CaH_2$ in solution in 550 ml of ethanol (water content<0.5%) was placed in a 2 liter reactor. The contents are heated to 27° C. and 97.4 g of TOSLEU (1 eq.) is added. The reaction is allowed to progress under good agitation for 4 hours. The mixture is filtered on a No. 4 sinter and the product formed into a (50/50) paste at 55° C. The whole is allowed to return to 15° C. and is filtered.
ρ=67%
OP=68%

2) Second step: Isolation of the enantiomer of aminopropanol

A concentrated solution of caustic soda is prepared (30 g of NaOH in 50 cc water).

The 41.73 g of tosylate is triturated with 50 ml of the caustic soda solution and is extracted 3 times with 100 g of $CH_2Cl_2$.

The filtrate is recovered and after extraction, the organic phase is put aside. The aqueous phase is treated 3 more times with 80 ml of $CH_2Cl_2$. The organic phases are collected together and dried over $Na_2SO_4$. The partially enriched mixture of enantiomers is recovered in the form of a yellow oil after evaporation under vacuum at 50° C.
ρ=83%
OP=68%

3) Third step: Preparation of the cinnamate of the (+) enantiomer of the aminopropanol.

7.2 g of the partially enriched mixture of enantiomers in 100 ml of di-isopropyl ether is put into a 250 ml flask. The contents are cooled to 0° C. and trans-cinnamic acid is added in small portions. The reaction is allowed to progress for 24 hours under good magnetic agitation. The solid is filtered on a No. 4 sinter; the mass recovered is 14.8 g (yield=69%), optical purity (OP) 82%.

The overall yield from the splitting reaction calculated as pure enantiomer is therefore 32%.

REFERENCES (1) Read, J. and I. G. M. Campbell, 1930, *J. Chem. Soc.*, 2682
(2) Green, A. L., R. Fielden, D. C. Bartlett, M. J. Cozens, R. J. Eden, D. W. Hills, 1967, *J. Med. Chem.*, 10, 1006.
(3) K. Rossen, P. M. Simpson, K. M. Wells, *Synthetic Comm.*, 23(8), 1071–1074 (1993): Synthesis of (R)-1-aminopropan-2-ol by means of decarboxylation of L-threonine.
(4) S. Wallbaum, T. Mehler and J. Martens, *Synthetic Comm.*, 24(10), 1381–1387, (1994): Synthesis of (R)-1-aminopropan-2-ol by means of decarboxylation of L-threonine.
(5) B. Koppenhoeffer, U. Trettin, A. Wächtler, *Synthesis*, 11, 1141–1142, (1994): Synthesis of (S) and (R)-1-amino-3-methylbutan-2-ol from D and L Valine.
(6) T. Ziegler, B. Hörsch and F. Effenberger, *Synthesis*, 575–578, (1990): Synthesis of 1-aminopentan-2-ol and 1-amino-3,3-dimethylbutan-2-ol from chiral cyanohydrin via enzymatic catalysis.
(7) R. Chinchilla, C. Najera and P. Sanchez-Agullo, *Tetrahedron Asymmetry*, 5, No. 7, 1393–1402, 1994: Enantioselective synthesis of 1-amino-4-methylpentan-2-ol via chiral nitroalcohol and by using chiral guanidine as catalyst.
(8) H. M. Wenghoefer, K. T. Lee, R. M. Srivastava, G. Srimannarayana and L. B. Clapp, *J. Heterocycl. Chem.*, 7, 6, 1407–1411, (1970): S(+)-1-aminobutan-2-ol from S(−)-1,2-epoxybutane.
(9) D. E. Wolf, W. H. Jones, J. Valiant, K. Folkers, *J. Am. Chem. Soc.*, 72, 2820, 1950: from Lactic acid.
(10) S. Yamazaki, S. Nagaya, K. Saito and T. Tanimura, *J. of Chromatography A*, 662, 219–225, (1994): from amino acid 1-aminopentan-2-ol and 1-aminohexan-2-ol.
(11) V. Gotor, R. Breva, F. Rebolledo, *J. Chem. Soc. Chem. Comm.*, 957–958 (1988): Enzymatic enantioselective acylation of 1-aminopropan-2-ol.

(12) R. L. Clark, W. H. Jones, W. J. Raich and K. Folkers, *J. Am. Chem. Soc.,* 76, 3995 (1954).

(13) R. H. Sullivan and N. J. Woodbary U.S. Pat. No. 3,116,332 (1963) and modifications of the method proposed in the experimental section of the publication of: G. Nieuwpoort and J. Reedijk, *Rec. Trav. Chim. Des Pays-Bas, J. of the Royal Netherlands Chemical Society,* 100, 378–382 (1981) (Resolution of 1-aminopropan-2-ol by means of fractional crystallization of diastereoisomeric salts).

(14) D. A. Milkovic, N. Sharaf El-Din, K. M. Gasi, *J. Chem. Soc.,* 50(6), 227–282, (1985): Resolution of 1-aminopropan-2-ol by means of fractional crystallization of diastereoisomeric salts.

(15) N. Sharaf El-Din, *Egypt. J. Chem.,* No. 3, 363–366, (1985) Resolution of 1-aminopropan-2-ol by means of fractional crystallization of diastereoisomeric salts.

(16) T. Shiraiwa, M. Nakamura, H. Nakagawa, N. Seike, S. Taniguchi, H. Kurokawa, *J. Chem. Soc. Of Japan,* 8, 1549–1555 (1985): Resolution of 1-aminopropan-2-ol by means of isothermal and seeded preferential crystallization.

(17) A. Kjaer, B. W. Christensen, S. E. Hansen, *Acta Chem. Scandinavica,* 13, 144–150, (1959): Resolution of 1-aminobutan-2-ol via fractional crystallization of 1-amino-3-buten-2-ol.

(18) L. Gajewczyk and A. Zejc, *Polish J. of Chemistry,* 64, 567–571, (1990): Resolution of 1-aminobutan-2-ol by means of derivatization and fractional crystallization of diastereoisomeric salts.

(19) C. A. Sprang and E. F. Degering, *J. Am. Chem. Soc.,* 64, 1063, (1963)

(20) S. W. Pelletier, *Chem. Ind.,* 1034, (1953).

(21) E. W. McChesney and W. M. Swann, *J. Am. Chem. Soc.,* 59, 1116–1118 (1937).

(22) D. Theodoropoulos and L. C. Craig, *J. Org. Chem.,* 21, 1376–1378, (1956).

What is claimed is:

1. A method of splitting 1-amino-alkan-2-ol compounds of general formula:

(I)

in which R represents linear, branched or cyclic alkyl groups, comprising from 1 up to about 25 carbon atoms, optionally having one or more double bonds, one or more hetero-atoms separated from the asymmetric carbon atom by at least one carbon link which do not destroy the aliphatic nature of R optionally substituted by one or more halogen atoms or lower alkoxy groups wherein the method comprises the steps of:

a) dissolving a racemic form of a compound of formula (I) and one of enantiomers R or S of N-tosyl-leucine, in pure alcohol, in suitable proportions, and then b) isolating the less soluble diastereoisomeric salt of the compound of formula (I) in crystallized form.

2. A method according to claim 1, characterized in that the diastereoisomeric salt of the compound of formula (I) obtained at step (b) is obtained by filtration or centrifugation.

3. A method according to claim 1 wherein after step (b), the method further comprises (c) treating the diastereoisomeric salt isolated at step (b) to obtain a first enantiomer of the compound of formula (I) to be split.

4. A method according to claim 3 wherein the treatment at step (c) comprises subjecting the diastereoisomeric salt obtained at step (b) to agitation in a basic medium and then extracting the first enantiomer of the compound of formula (I) to be split with an organic solvent.

5. A method according to claim 1 wherein at step (a) about from 0.5 to 1 molar equivalents of one of R or S enantiomers of N-tosyl-leucine is dissolved for each 1 mole of compound of formula (I) to be split.

6. A method according to claim 1 further comprising the step of (c') treating mother solutions resulting from isolation of the diastereoisomeric salt from step (b) to obtain the second enantiomer of the compound of formula (I) to be split.

7. A method according to claim 6, wherein the treatment in step (c') comprises subjecting the mother solutions to evaporation and then treating residue resulting from the evaporation with a basic solution and extracting, with $CH_2Cl_2$, the second enantiomer of the compound of formula (I) to be split.

8. A method according to claim 6 further comprising the step of (d) producing a cinnamate of the second enantiomer by addition to said second enantiomer obtained at step (c') of about 1 equivalent of trans-cinnamic acid and then carrying out a recrystallization with ethanol.

9. A method according to claim 8, wherein addition of trans-cinnamic acid at step (d) forms a conglomerate, and wherein said method further comprises subsequent step (e) of preferential crystallization, by selectively dissolving a part of the crystals from step (d) in a solution of the racemic mixture in the form of cinnamate, prepared as in step (d), in ethanol to obtain an equilibrium between the saturated solution and the crystals of the cinnamate of the second enantiomer and then cooling and afterwards filtering the suspension to obtain a total initial mass of enantiomer greater than the enantiomeric excess with a high optical purity and, optionally, adding the racemic mixture in a quantity equal to that of the enantiomer obtained to isolate, in turn, first one and then the other enantiomer of the cinnamate of the amino-alcohol.

10. A method according to claim 1 wherein:

the 1-aminoalkan-2-ol is 1-aminopropan-2-ol; and wherein during step a) suitable proportions comprise 1 equivalent of 1-aminopropan-2-ol and from 0.5 to 1 equivalent of one of the enantiomers R or S of N-tosyl-leucine are dissolved with a concentration of 19% by mass in a waterless organic solvent;

said isolating step b) further comprises, after 4 hours agitation, filtering the suspension to recover the pure diastereoisomeric salt, after washing or recrystallization in absolute ethanol; and further comprising the steps of:

c) treating the salt with a saturated solution of NaOH, and extracting the first enantiomer of the 1-aminopropan-2-ol with $CH_2Cl_2$; wherein the organic phases are brought together, dried with $Na_2SO_4$ and then evaporated to obtain the first enantiomer of 1-aminopropan-2-ol;

c') evaporating the mother liquors from the crystallization in step b) to obtain the second enantiomer of 1-aminopropan-2-ol;

d) purifying said second enantiomer by producing its cinnamate in stoichiometric fashion in di-isopropyl ether followed by several recrystallizations in ethanol;

e) selectively dissolving a portion of the crystals from step (d) in a 24.5% by mass solution of a racemic mixture in the form of cinnamate, prepared as in step (d), in ethanol to obtain an equilibrium between the saturated solution and the crystals of the cinnamate of the second enantiomer of 1-aminopropan-2-ol; wherein the suspension is cooled and then filtered to obtain a total initial mass of enantiomer greater than the enantiomeric excess with a high optical purity; and wherein the racemic mixture can then be added at a quantity equal to that of the enantiomer obtained to isolate, in turn, first one and then the other enantiomer of the cinnamate of 1-aminopropan-2-ol.

11. The method according to claim 1 wherein:

the 1-aminoalkan-2-ol is 1-aminobutan-2-ol; and wherein during step (a) suitable proportions comprise, 1 equivalent of 1-aminobutan-2-ol and from 0.5 to 1 equivalent of one of the enantiomers R or S of N-tosyl-leucine are dissolved with a concentration of 7% by mass in a waterless organic solvent;

said isolating step (b) further comprises, after 4 hours agitation, filtering the suspension to recover the pure diastereoisomeric salt, after washing or recrystallization in absolute ethanol; and further comprising the steps of:

(c) treating the salt with a saturated solution of NaOH, then extracting the first enantiomer of the 1-aminobutan-2-ol with $CH_2Cl_2$ wherein the organic phases are brought together, dried with $Na_2SO_4$ and then evaporated to obtain the first enantiomer of 1-aminobutan-2-ol;

(c') evaporating the mother liquors from the crystallization in step b) to obtain the second enantiomer of 1-aminobutan-2-ol;

(d) purifying said second enantiomer by producing its cinnamate in stoichiometric fashion in di-isopropyl ether followed by several recrystallizations in ethanol.

12. The method according to claim 1 wherein:

the 1-aminoalkan-2-ol is 1-aminopentan-2-ol; and wherein during step a), the suitable proportions comprise 1 equivalent of 1-aminopentan-2-ol and from 0.5 to 1 equivalent of one of the enantiomers R or S of N-tosyl-leucine are dissolved with a concentration of 15% by mass in a waterless organic solvent;

said isolating step b), further comprises, after 4 hours agitation, filtering the suspension to recover the pure diastereoisomeric salt, after washing or recrystallization in absolute ethanol; and further comprising the steps of:

c) treating the salt with a saturated solution of NaOH, then extracting the first enantiomer of the 1-aminopentan-2-ol with $CH_2Cl_2$; wherein the organic phases are brought together, dried with $Na_2SO_4$ and then evaporated to obtain the first enantiomer of 1-aminopentan-2-ol;

c') evaporating the mother liquors from the crystallization in step b) to obtain the second enantiomer of 1-aminopentan-2-ol d) purifying said second enantiomer by producing its cinnamate in stoichiometric fashion in di-isopropyl ether followed by several recrystallizations in ethanol;

e) selectively dissolving a portion of the crystals from step (d) in a 15.1% by mass solution of racemic mixture in the form of cinnamate, prepared as in step (d), in ethanol to obtain an equilibrium between the saturated solution and the crystals of the cinnamate of the second enantiomer of 1-aminopentan-2-ol, wherein this suspension is cooled and then filtered to obtain a total initial mass of enantiomer greater than the enantiomeric excess with a high optical purity, wherein the racemic mixture can then be added at a quantity equal to that of the enantiomer obtained to isolate, in turn, first one and then the other enantiomer of the cinnamate of 1-aminopentan-2-ol.

13. The method according to claim 1 wherein:

the 1-aminoalkan-2-ol is 1-amino-3-methylbutan-2-ol; and wherein during step a), suitable proportions comprise 1 equivalent of 1-amino-3 -methylbutan-2-ol and from 0.5 to 1 equivalent of one of the enantiomers R or S of N-tosyl-leucine are dissolved with a concentration of the order of 9% by mass in a waterless organic solvent;

isolation step b) further comprises, after 4 hours agitation, filtering the suspension to recover the pure diastereoisomeric salt, after washing or recrystallization in absolute ethanol; and further comprising the steps of:

c) treating the salt with a saturated solution of NaOH, then extracting the first enantiomer of the 1-amino-3-methylbutan-2-ol with $CH_2Cl_2$, wherein the organic phases are brought together, dried with $Na_2SO_4$ and then evaporated to obtain the first enantiomer of 1-amino-3-methylbutan-2-ol;

c') evaporating the mother liquors from the crystallization in step b) to obtain the second enantiomer of 1-amino-3-methylbutan-2-ol;

d) purifying said second enantiomer by producing its cinnamate in stoichiometric fashion in di-isopropyl ether followed by several recrystallizations in ethanol e) selectively dissolving a portion of the crystals from step (d) in a 15.0% by mass solution of racemic mixture in the form of cinnamate, prepared as in step (d), in ethanol to obtain an equilibrium between the saturated solution and the crystals of the cinnamate of the second enantiomer of 1-amino-3-methylbutan-2-ol; wherein the suspension is cooled and then filtered to obtain a total initial mass of enantiomer greater than the enantiomeric excess with a high optical purity, wherein the racemic mixture can then be added at a quantity equal to that of the enantiomer obtained to isolate, in turn, first one and then the other enantiomer of the cinnamate of 1-amino-3-methylbutan-2-ol.

14. The method according to claim 1 wherein:

the 1-aminoalkan-2-ol is 1-aminohexan-2-ol; and wherein during step a) suitable proportions comprise 1 equivalent of 1-aminohexan-2-ol and from 0.5 to 1 equivalent of one of the enantiomers R or S of N-tosyl-leucine are dissolved with a concentration of 12% by mass in a waterless organic solvent;

isolating step b) further comprises, after 4 hours agitation, filtering the suspension to recover the pure diastereoisomeric salt, after washing or recrystallization in absolute ethanol; and further comprising the steps of:

c) treating the salt with a saturated solution of NaOH, then extracting the first enantiomer of the 1-aminohexan-2-ol with $CH_2Cl_2$, wherein the organic phases are brought together, dried with $Na_2SO_4$ and then evaporated to obtain the first enantiomer of 1-aminohexan-2-ol;

c') evaporating the mother liquors from the crystallization in step b) to obtain the second enantiomer of 1-aminohexan-2-ol;

d) purifying said second enantiomer by producing its cinnamate in stoichiometric fashion in di-isopropyl ether followed by several recrystallizations in ethanol;

e) selectively dissolving a portion of the crystals from step (d) in a 15.0% by mass solution of racemic mixture in the form of cinnamate, prepared as in step (d), in ethanol to obtain an equilibrium between the saturated solution and the crystals of the cinnamate of the second enantiomer of 1-aminohexan-2-ol, wherein this suspension is cooled and then filtered to obtain a total initial mass of enantiomer greater than the enantiomeric excess with a high optical purity, wherein the racemic mixture can then be added at a quantity equal to that of the enantiomer obtained to isolate, in turn, first one and then the other enantiomer of the cinnamate of 1-aminohexan-2-ol.

15. The method according to claim 1 wherein
the 1-aminoalkan-2-ol is 1-amino-4-methylpentan-2-ol; and wherein
during step a) suitable proportions comprise 1 equivalent of 1-amino-4-methylpentan-2-ol and from 0.5 to 1 equivalent of one of the enantiomers R or S of N-tosyl-leucine are dissolved with a concentration of 9% by mass in a waterless organic solvent;
isolating step b) further comprises after 4 hours agitation, filtering the suspension to recover the pure diastereoisomeric salt, after washing or recrystallization in absolute ethanol; and further comprising the steps of:
c) treating the salt with a saturated solution of NaOH, then extracting the first enantiomer of the 1-amino-4-methylpentan-2-ol with $CH_2Cl_2$, wherein the organic phases are brought together, dried with $Na_2SO_4$ and then evaporated to obtain the first enantiomer of 1-amino-4-methylpentan-2-ol;
c') evaporating the mother liquors from the crystallization in step b) to obtain the second enantiomer of 1-amino-4-methylpentan-2-ol;
d) purifying said second enantiomer by producing its cinnamate in stoichiometric fashion in di-isopropyl ether followed by several recrystallizations in ethanol;
e) selectively dissolving a portion of the crystals from step (d) in a 15.1% by mass solution of racemic mixture in the form of cinnamate, prepared as in step (d), in ethanol in order to obtain an equilibrium between the saturated solution and the crystals of the cinnamate of the second enantiomer of 1-amino-4-methylpentan-2-ol, wherein this suspension is cooled and then filtered to obtain a total initial mass of enantiomer greater than the enantiomeric excess with high optical purity, wherein the racemic mixture can then be added at a quantity equal to that of the enantiomer obtained to isolate, in turn, first one and then the other enantiomer of the cinnamate of 1-amino-4-methylpentan-2-ol.

16. The method according to claim 1 wherein:
the 1-aminoalkan-2-ol is 1-amino-3,3-dimethylbutan-2-ol, and wherein
during step a) suitable proportions comprise 1 equivalent of 1-amino-3,3-dimethylbutan-2-ol and from 0.5 to 1 equivalent of one of the enantiomers R or S of N-tosyl-leucine are dissolved with a concentration of 9% by mass in a waterless organic solvent;
isolating step b) further comprises, after 4 hours agitation, filtering the suspension to recover the pure diastereoisomeric salt, after washing or recrystallization in absolute ethanol; and further comprising the steps of:
c) treating the salt with a saturated solution of NaOH, then extracting the first enantiomer of the 1-amino-3,3-dimethylbutan-2-ol with $CH_2Cl_2$ wherein the organic phases are brought together, dried with $Na_2SO_4$ and then evaporated to obtain the first enantiomer of 1-amino-3,3-dimethylbutan-2-ol;
c') evaporating the mother liquors from the crystallization in step b) to obtain the second enantiomer of 1-amino-3,3-dimethylbutan-2-ol.

17. The method according to claim 1 wherein:
the 1-aminoalkan-2-ol is 1-aminoheptan-2-ol; and wherein
during step a) suitable proportions comprise 1 equivalent of 1-aminoheptan-2-ol and from 0.5 to 1 equivalent of one of the enantiomers R or S of N-tosyl-leucine are dissolved with a concentration of 9% by mass in a waterless organic solvent;
isolating step b) further comprises, after 4 hours agitation, filtering the suspension to recover the pure diastereoisomeric salt, after washing or recrystallization in absolute ethanol; and further comprising the steps of:
c) treating the salt with a saturated solution of NaOH, then extracting the first enantiomer of the 1-aminoheptan-2-ol. wherein the organic phases are brought together, dried with $Na_2SO_4$ and then evaporated to obtain the first enantiomer of 1-aminoheptan-2-ol.
c') evaporating the mother liquors from the crystallization in step b) to obtain the second enantiomer of 1-aminoheptan-2-ol.

18. The method according to claim 1 wherein:
the 1-aminoalkan-2-ol is 1-amino-3-ethylpentan-2-ol; and wherein
during step a) further comprises, 1 equivalent of 1-amino-3-ethylpentan-2-ol and from 0.5 to 1 equivalent of one of the enantiomers R or S of N-tosyl-leucine are dissolved with a concentration of 2% by mass in a waterless organic solvent;
isolating step b) further comprises after 4 hours agitation, filtering the suspension to recover the pure diastereoisomeric salt, after washing or recrystallization in absolute ethanol; and further comprising the steps of:
c) treating the salt with a saturated solution of NaOH, then extracting the first enantiomer of the 1-amino-3-ethylpentan-2-ol with $CH_2Cl_2$, wherein the organic phases are brought together, dried with $Na_2SO_4$ and then evaporated to obtain the first enantiomer of 1-amino-3-ethylpentan-2-ol;
c') evaporating the mother liquors from the crystallization in step b) to obtain the second enantiomer of 1-amino-3-ethylpentan-2-ol.

19. The method according to claim 1 wherein:
the 1-aminoalkan-2-ol is 1-amino-2-cyclohexylethan-2-ol; and wherein
during step a) suitable proportions 1 equivalent of 1-amino-2-cyclohexylethan-2-ol and from 0.5 to 1 equivalent of one of the enantiomers R or S of N-tosyl-leucine are dissolved with a concentration of 4% by mass in a waterless organic solvent;
isolating step b) further comprises after 4 hours agitation, filtering the suspension to recover the pure diastereoisomeric salt, after washing or recrystallization in absolute ethanol; and further comprising the steps of:
c) treating the salt with a saturated solution of NaOH, then extracting the first enantiomer of the 1-amino-2-cyclohexylethan-2-ol with $CH_2CL_2$, wherein the organic phases are brought together, dried with $Na_2SO_4$ and then evaporated to obtain the first enantiomer of 1-amino-2-cyclohexylethan-2-ol;

c') evaporating the mother liquors from the crystallization in step b) to obtain the second enantiomer of 1-amino-2-cyclohexylethan-2-ol;

d) purifying said second enantiomer by producing its cinnamate in stoichiometric fashion in di-isopropyl ether followed by several recrystallizations in ethanol;

e) selectively dissolving a portion of the crystals from step (d) in an 8.2% by mass solution of racemic mixture in the form of cinnamate, prepared as in step (d), in ethanol to obtain an equilibrium between the saturated solution and the crystals of the cinnamate of the second enantiomer of 1-amino-2-cyclohexylethan-2-ol; wherein suspension is cooled and then filtered to obtain a total initial mass of enantiomer greater than the enantiomeric excess with a high optical purity, Still with step (e), the racemic mixture can then be added at a quantity equal to that of the enantiomer obtained to isolate, in turn, first one and then the other enantiomer of the cinnamate of 1-amino-2-cyclohexylethan-2-ol.

20. A method according to claim 1 further comprising after step (b), a strong acidification step to recover the R or S enantiomer of N-tosyl-leucine.

21. A method for splitting a 1-aminoalkan-2-ol of general formula:

(I)

in which R represents linear, branched or cyclic alkyl groups comprising from 1 up to about 25 carbon atoms;

comprising the step of utilizing one of the enantiomers R or S of N-tosyl-leucine.

22. A method of splitting chiral 1-aminoalkan-2-ol compounds utilizing a trans-cinnamate of an enantiomer of a chiral 1-aminoalkan-2-ol compound for the purification, without loss of the enantiomeric excess, of said enantiomer.

23. A method for splitting chiral 1-aminoalkan-2-ol compounds utilizing a trans-cinnamate of an enantiomer of a chiral 1-aminoalkan-2-ol compound for the formation of a conglomerate allowing the recovery of the enantiomeric excess by recrystallization methods.

* * * * *